United States Patent [19]

Butterfield

[11] Patent Number: 4,493,703
[45] Date of Patent: Jan. 15, 1985

[54] HYPODERMIC SYRINGE CARTRIDGE WITH NON-RETRACTABLE DRIVE PISTON

[75] Inventor: Ida M. Butterfield, Santa Maria, Calif.

[73] Assignee: Butterfield Group, Santa Maria, Calif.

[21] Appl. No.: 609,520

[22] Filed: May 14, 1984

Related U.S. Application Data

[63] Continuation-in-part of Ser. No. 542,084, Oct. 17, 1983, abandoned, which is a continuation of Ser. No. 363,927, Mar. 31, 1982, abandoned.

[51] Int. Cl.³ .............................................. A61M 5/00
[52] U.S. Cl. .................................................. 604/110
[58] Field of Search ............... 604/110, 111, 218, 219, 604/220, 221, 222, 228, 183, 93, 38

[56] References Cited

U.S. PATENT DOCUMENTS

| 2,753,867 | 7/1956 | Goldberg | 604/228 |
| 3,742,949 | 7/1973 | Hill | 128/218 PA |
| 4,233,975 | 11/1980 | Yerman | 128/218 P |
| 4,367,738 | 1/1983 | Legendre et al. | 604/218 |

*Primary Examiner*—John D. Yasko
*Attorney, Agent, or Firm*—Daniel C. McKown

[57] ABSTRACT

The drive piston of a hypodermic syringe is rendered non-retractable by including on it a resilient disc-like element whose free diameter is slightly larger than the diameter of the glass tubular body of the syringe. The drive piston is inserted into the glass tubular body from the rear end, thereby causing the resilient disc-like element to become dished with its concave side facing rearward. The dished resilient element acts as a continuous pawl since any attempt to retract the drive piston jams the edge of the resilient element against the inside wall of the tubular body.

2 Claims, 3 Drawing Figures

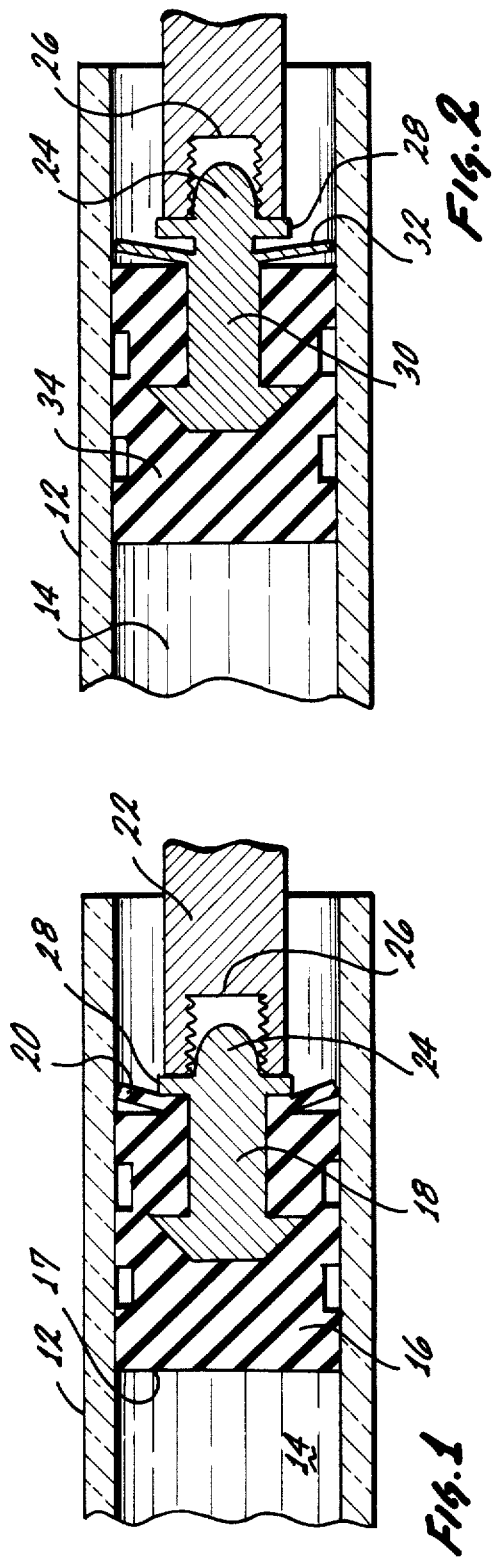
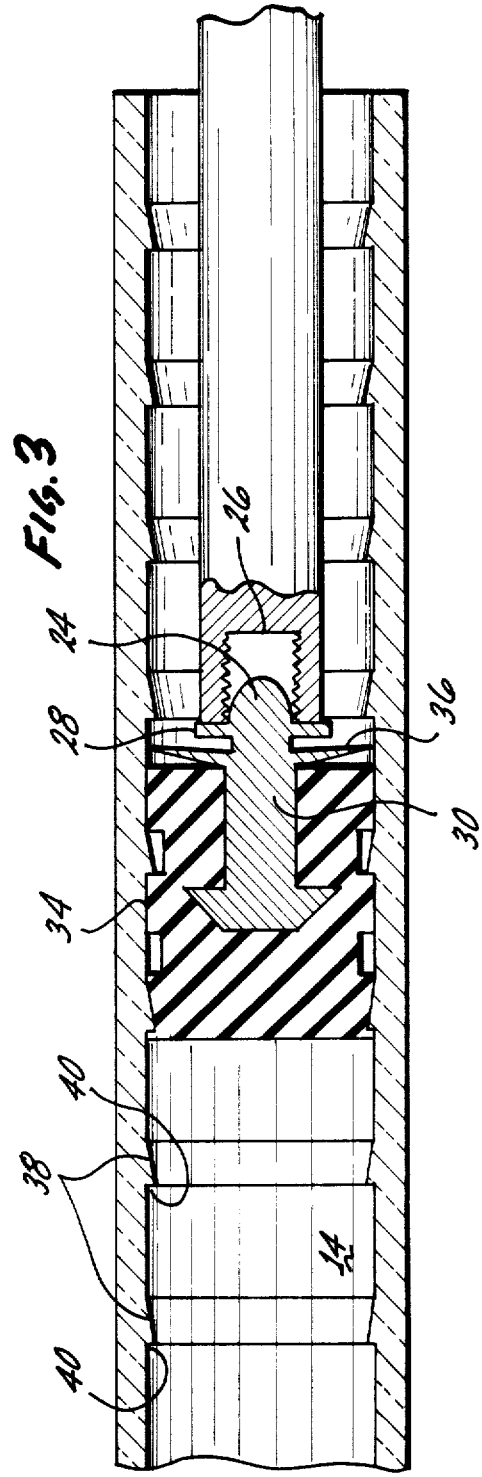

HYPODERMIC SYRINGE CARTRIDGE WITH NON-RETRACTABLE DRIVE PISTON

This application is a continuation of application Ser. No. 542,084 filed Oct. 17, 1983, now abandoned which was a continuation of application Ser. No. 363,927 filed Mar. 31, 1982, now abandoned. The benefit of the filing date of the original application, Mar. 31, 1982, is hereby claimed for the present application.

BACKGROUND OF THE INVENTION

1. Field of the Invention The present invention is in the field of medical equipment, and more specifically relates to a cartridge for a hypodermic syringe, the cartridge having a drive piston that can be moved only in one direction.

2. The Prior Art

Unless fluid mediciments are to be mixed in the syringe, there is no reason why the drive piston should be retractable. That is, since fluid is only removed from the syringe it is necessary only that the drive piston be advanceable, but there is no need for the drive piston to be retractable.

Cartridges for syringes known in the prior art include a tubular glass member within which a drive piston of soft rubber slides in sealing engagement. Motion is transmitted by the user to the drive piston by means of an actuator rod which is removably attached to a metal screw that is embedded in the rubber drive piston and that extends from the back side of the rubber drive piston. It is generally desirable that the resistance of the drive piston to advancement be substantially constant as opposed to intermittent.

The use of a pawl in devices other than hypodermic syringes to prevent motion in one direction while permitting motion in the opposite direction is well known. However, the problems attendant to adapting a pawl for use in a hypodermic syringe seem to be insurmountable because a pawl must be associated with a toothed surface, and such a surface would seem to have no place inside the tubular member of the cartridge.

The principle of a continuous ratchet can be demonstrated by the use of a pencil having an eraser on one end. The eraser of the pencil should touch the top of the desk and the shaft of the pencil should be inclined to the desk at an angle of approximately 60° or greater. It will then be found difficult to push the eraser across the desk, but easy to draw the eraser in the direction indicated by the point of the pencil. This principle is applied in a well-known type of doorstop, but it was by no means apparent how this physical principle could be put to use in the cartridge of a hypodermic syringe.

SUMMARY OF THE INVENTION

The present inventor has succeeded in applying the above-described physical principle of a continuous ratchet to produce a drive piston that can be moved in only one direction within the tubular member of the cartridge of a hypodermic syringe. This is accomplished by affixing to the drive piston a resilient member that has a diameter slightly greater than the diameter of the bore of the tubular member, so that when the drive piston is inserted into the tubular member, the element is forced to assume a dished shape, which is convex in the direction of intended motion.

The present inventor recognized that the holding power of such a dished element could conceivably be overpowered by brute force, or, alternatively, a lubricant could be applied to the inside wall of the tubular member to reduce the holding power of the element. These potential problems were overcome by combining the dished element with an actuator rod that is not attached to the drive piston and that therefore can push the drive piston but cannot retract it.

The novel features which are believed to be characteristic of the invention, both as to organization and method of operation, together with further objects and advantages thereof, will be better understood from the following description considered in connection with the accompanying drawings in which several embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a fractional cross-sectional view of a first preferred embodiment of the hypodermic syringe cartridge of the present invention;

FIG. 2 is a fractional cross-sectional view of a second preferred embodiment of the cartridge in accordance with the present invention; and FIG. 3 is a fractional cross-sectional view of a third preferred embodiment of the cartridge of the present invention.

DETAILED DESCRIPTION OF THE PREFERRED EMBODIMENTS

FIG. 1 shows a first preferred embodiment of the invention in which a drive piston 16 forms a slidable seal within the tubular member 12 so that as the drive piston 16 is advanced to the left in FIG. 1, some of the fluid 14 will be expelled from the hypodermic syringe. The drive piston 16 differs from drive pistons known in the prior art by the presence of an integral disc 20 whose central portion joins the remainder of the drive piston 16. In the preferred embodiment, the disc 20 is composed of the same material as the resilient portion of the drive piston 16, preferably a soft rubber. The diameter of the disc 20 is slightly larger than the diameter of the bore of the tubular member 12 so that the disc 20 is forced into a dish-like shape that is convex toward the leading end 17 of the drive piston, i.e., in the direction of the intended motion.

The drive piston 16 includes an insert 18 which is useful for distributing the force applied by the actuator rod 22. The actuator rod 22 is not normally a part of the cartridge and includes a threaded hole at its front end, which normally engages a threaded shank of an insert of a type known in the prior art. Unlike the prior art insert, the insert of the present invention has an unthreaded shank 24 small enough in diameter to pass freely into the threaded hole 26 in the actuator rod 22. The insert 18 also includes a circular flange 28 against which the end of the actuator rod 22 bears. The ogival shape of the unthreaded shank 24 deters tampering because it is difficult to grip.

In operation, the actuator rod is slipped over the unthreaded shank 24 by the user and is pushed to the left in FIG. 1 thereby forcing the drive piston 16 to move towards the left. The disc 20 produces a smooth drag force of relatively small magnitude as the drive piston 16 moves to the left. Because the threaded hole 26 in the actuator rod 22 slips loosely over the unthreaded shank 24 of the insert 18, the actuator rod 22 will disengage from the insert 18 when the actuator rod is pulled to the right in FIG. 1. If an attempt is made to defeat this feature by putting a sticky material in the threaded hole 26, it will be found that the disc 20 jams against the inside walls of the tubular member 12 and thus produces a substantial force opposing motion of the drive piston 16 to the right in FIG. 1. This force is sufficiently great that it causes the sticky material introduced into the threaded hole 26 to yield, thereby releasing the actuator rod 22. The unthreaded shank 24 serves to center and to steady the actuator rod in normal usage.

FIG. 2 shows a second preferred embodiment of the present invention in which the insert 30 includes a disc 32 that not only serves the same purpose as the disc 20 of FIG. 1, but which also forms an impenetable barrier to prevent penetration of the drive piston 34 by a hypodermic needle for the purpose of pilfering the fluid 14 in the cartridge. In the second preferred embodiment shown in FIG. 2, the disc 32 is an integral part of the insert 30 and preferably is made of a resilient metal. The resilient portion of the drive piston 34 is substantially the same as a drive piston used in the prior art.

In operation, when an attempt is made to pull the drive piston 34 of FIG. 2 to the right, the disc 32 jams against the inside wall of the tubular member 12 thereby strongly resisting any further motion of the drive piston toward the right.

FIG. 3 shows a third preferred embodiment of the invention which is similar to that of FIG. 2, but in which the inside surface of the tubular member 12 includes a number of longitudinally-spaced ratchet teeth of which the teeth 38 are typical.

As the drive piston 34 is moved to the left, the disc-like element 36 flexes to permit the motion. However, if an attempt is made to move the drive piston 34 to the right, the disc-like element 36 will engage one of the faces 40 of the ratchet teeth 38 thereby preventing motion of the drive piston to the right.

The embodiment of FIG. 3 has a more positive ratchet action than the embodiments of FIGS. 1 and 2, but it is believed that such a strong ratchet action is not required unless the actuator rod 22 is attached to the insert 30. It is believed that the embodiment of FIG. 3 would be more difficult to manufacture than the embodiments of FIGS. 1 and 2, and to that extent, the embodiment of FIG. 3 would be less preferred. The embodiment of FIG. 3, like the embodiment of FIG. 2, does provide an impenetrable disc to prevent pilferage of the fluid 14 by insertion of a hypodermic needle through the drive piston 34.

It is recognized that the element described as a disc 20 of FIG. 1 could be replaced by one or more finger-like projections; similar considerations apply to the disc 32 of FIG. 2 and the disc-like element 36 of FIG. 3. The use of a disc, as opposed to fingers, is preferable for preventing pilferage, as discussed above.

The disc-like elements 20 of FIG. 1, 32 of FIG. 2 and 36 of FIG. 3 could probably be overpowered by the application of brute force pushing the piston to the right in all of the figures, but this is prevented by use of the unthreated shank 24 which prevents the actuator rod from being attached to the insert.

When the drive piston 34 of the embodiment of FIG. 3 is moved to the left, the user can feel varying degrees of resistance, and this may be helpful to the user as an indicator of the amount of fluid injected.

Thus, there has been described a cartridge for a hypodermic syringe, which cartridge has a drive piston that can be moved only in one direction. Several embodiments and variations of the invention have been disclosed, and it is to be understood that additional embodiments and variations will be obvious to those skilled in the art. The embodiments described herein together with those additional variations are considered to be within the scope of the invention.

What is claimed is:

1. An insert, part of which is permanently embedded within the drive piston that is pushed by an actuating rod within the tubular member of a hypodermic syringe to expel fluid from the hypodermic syringe, characterized in that said insert simultaneously serves the dual purposes of preventing retraction of the drive piston from any position along the tubular member to which the drive piston has been advanced and of preventing penetration of the drive piston by a hypodermic needle, thereby rendering the hypodermic syringe pilfer-proof, said insert comprising:
   a resilient element spanning the bore of the tubular member when inside the tubular member, impenetrable by a hypodermic needle, and extending radially when removed from the tubular member to a diameter greater than the bore of the tubular member so that peripheral portions of said resilient element are forced to bow rearward when the drive piston is inserted into the tubular member from the rear;
   said peripheral portions frictionally contacting the inside wall of the tubular member, the friction between said peripheral portions and the inside wall resisting rearward motion of the drive piston at all positions of the drive piston within the tubular member so that any attempt to pull the drive piston toward the rear of the tubular member will force said peripheral portions to jam even more tightly against the inside wall of the tubular member, thereby preventing retraction of the drive piston at all positions of the drive piston within the tubular member.

2. The insert of claim 1 serving the additional purpose of positioning the tip of the actuating rod at the center of the drive piston, and comprising;
   a shank portion extending rearward beyond the drive piston and centered on the axis of the drive piston.

* * * * *